US 9,199,029 B2
(12) United States Patent
Daly

(10) Patent No.: US 9,199,029 B2
(45) Date of Patent: Dec. 1, 2015

(54) FLUSHABLE INJECTION PORT

(75) Inventor: Geoffrey Daniel Daly, Sherwood (AU)

(73) Assignee: Analytica Limited, Queensland (AU)

( * ) Notice: Subject to any disclaimer, the term of this patent is extended or adjusted under 35 U.S.C. 154(b) by 440 days.

(21) Appl. No.: 13/000,118

(22) PCT Filed: Apr. 30, 2009

(86) PCT No.: PCT/AU2009/000550
§ 371 (c)(1),
(2), (4) Date: Dec. 20, 2010

(87) PCT Pub. No.: WO2009/152555
PCT Pub. Date: Dec. 23, 2009

(65) Prior Publication Data
US 2011/0112485 A1 May 12, 2011

(30) Foreign Application Priority Data
Jun. 20, 2008 (AU) .................. 2008903153

(51) Int. Cl.
A61M 5/14 (2006.01)
A61M 39/26 (2006.01)
A61M 39/02 (2006.01)

(52) U.S. Cl.
CPC ............. *A61M 5/14* (2013.01); *A61M 5/1412* (2013.01); *A61M 39/26* (2013.01); *A61M 2005/1403* (2013.01); *A61M 2039/0202* (2013.01); *A61M 2039/0205* (2013.01)

(58) Field of Classification Search
CPC ............. A61M 2005/1403; A61M 2039/0202; A61M 2039/0205; A61M 39/26; A61M 5/14; A61M 5/1412
USPC ........................................ 604/181, 246–256
See application file for complete search history.

(56) References Cited

U.S. PATENT DOCUMENTS

| 3,993,066 | A | * | 11/1976 | Virag ............................. 604/518 |
| 4,256,103 | A | * | 3/1981 | Mylrea .......................... 604/81 |
| 4,548,600 | A | | 10/1985 | Ruschke |
| 2003/0018308 | A1 | | 1/2003 | Tsai |

FOREIGN PATENT DOCUMENTS

| CN | 2413719 Y | 1/2001 |
| EP | 1535638 A1 | 6/2005 |
| GB | 2104862 A | 3/1983 |
| WO | 8707158 A1 | 12/1987 |
| WO | 2009152555 A1 | 12/2009 |

OTHER PUBLICATIONS

Chinese Office Action with translation dated Aug. 17, 2012, Application No. 200980121636.9, 16 pages.

* cited by examiner

*Primary Examiner* — Imani Hayman

(57) ABSTRACT

The combination (10) of a burette (11) and injection portion (20) and a tube (21) to be connected to a reservoir to drain a liquid therefrom for delivery to the burette (11). The injection port (20) is fixed to a cap (16) of the burette (11) by having an outlet (28) extending to and being secured to an inlet (19) of the burette (11).

4 Claims, 3 Drawing Sheets

FLUSHABLE INJECTION PORT

CROSS-REFERENCE TO RELATED APPLICATION

This Application claims the benefit of PCT Application No. PCT/AU2009/000550 filed on Apr. 30, 2009, entitled "A FLUSHABLE INJECTION PORT," which claims the benefit of Australian Provisional Application No. 2008903153 filed on Jun. 20, 2008, which are commonly assigned with the present invention and incorporated herein by reference.

TECHNICAL FIELD

The present invention relates to injection ports to deliver a medication to a patient via an intravenous tubing set that includes a length of tubing extending to a needle that is implanted in the patient. A typical example of this arrangement is described in U.S. Pat. No. 5,782,816.

BACKGROUND OF THE INVENTION

In certain hospitals the above discussed arrangement requires the health care professional involved to use a small saline vial to flush the injection site to ensure that all medication is delivered to the patient. If not flushed, the residual medication is wasted not only from an expense point of view but also from a patient care point of view.

The above discussed arrangement of flushing the injection site has the disadvantage that the healthcare professional must not only provide a vial but is also required to undertake further steps when delivering medication through an injection port. This increases the cost of delivering medication as well as the taken time to flush the site. A further disadvantage is the increased risk of infection due to the changing of connections.

OBJECT OF THE INVENTION

It is the object of the present invention to overcome or substantially ameliorate at least one of the above disadvantages.

SUMMARY OF THE INVENTION

There is disclosed herein in combination a burette, a tube to connect the burette to a reservoir containing a first liquid, and an injection port:

said burette having an outlet via which an outward liquid is to be delivered to a patient, an inlet via which said tube delivers the first liquid to said burette;

said tube having an end portion for connection to the reservoir to provide for draining of the first liquid from the reservoir; and said injection port being located downstream of said end portion and upstream of said outlet, said port having a chamber, an inlet to receive said first liquid from said tube and to deliver the first liquid to said chamber, an injection inlet via which a second liquid is delivered to said chamber, and an outlet providing for communication between said chamber and said burette for delivering the first and second liquid to said burette for delivery from the burette via said outlet as said outlet liquid.

Preferably, said injection inlet includes a closure operable to be opened for the delivery of said second liquid to said chamber but urged to a closed position closing said chamber.

Preferably, said injection port is connected to said burette by a further tube.

In an alternative preferred form, said injection port is mounted on said burette.

In a still further alternative form, said burette has a hollow body to receive the first and second liquids, and a upper part closing said body, with said injection port being incorporated in said upper part.

Preferably, said upper part includes a duct connected to said tube and in communication with said first inlet for the delivery of said first liquid to said chamber.

BRIEF DESCRIPTION OF THE DRAWINGS

Preferred forms of the present invention will now be described by way of example with reference to the accompanying drawings wherein.

DETAILED DESCRIPTION OF THE PREFERRED EMBODIMENTS

Figures 1, 2, 3:
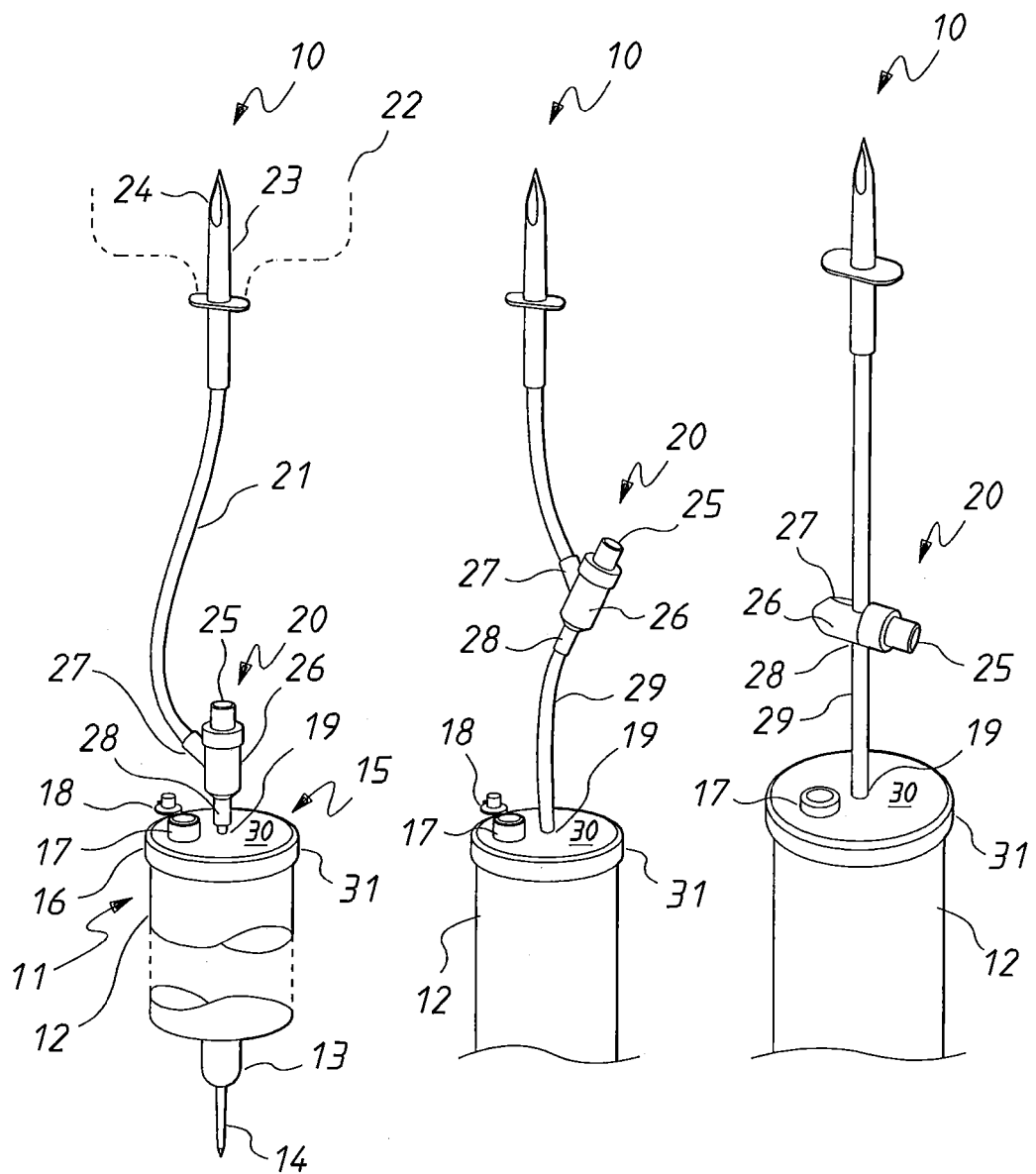
FIG. 1 is a schematic pictorial view of a combination including a burette, injection port and tube to connect the injection port to a reservoir.
FIG. 2 is a schematic pictorial view of a modification of the combination of claim 1.
FIG. 3 is a schematic pictorial view of a further modification of the combination of claim 1.

In the accompanying drawings there is schematically depicted various embodiments of a combination 10. Each combination 10 includes a burette 11. As an example, the burette 11 may be the burette described in International Patent Application PCT/AU2006/001495 (International Publication No. WO 2007/041787). The burette 11 may also be as per International Standard ISO 8536-5:2004. The burette 11 has an outer body 12 that extends to an outlet 13 from which a tube 14 extends to the patient, more particularly an intravenous tube. The upper portion 15 of the burette 11 includes a cap 16 sealingly engaged with the body 12. The cap 16 includes a port 17 closable by means of a plug 18 movably secured to the port 17. The cap 16 further includes a burette inlet 19 to which there is attached an injection port 20. The injection port 20 is also attached to a tube 21 extending to a reservoir 22. Typically the reservoir is a bag having a lower end into which there projects an end portion 23 of the tube 21. The end portion 23 has an inlet 24 via which a liquid contained in the reservoir 22 enters the tube 21 for delivery to the injection port 20. If required a clamp (not illustrated) may be applied to the tube 21 to regulate flow.

Figure 7:
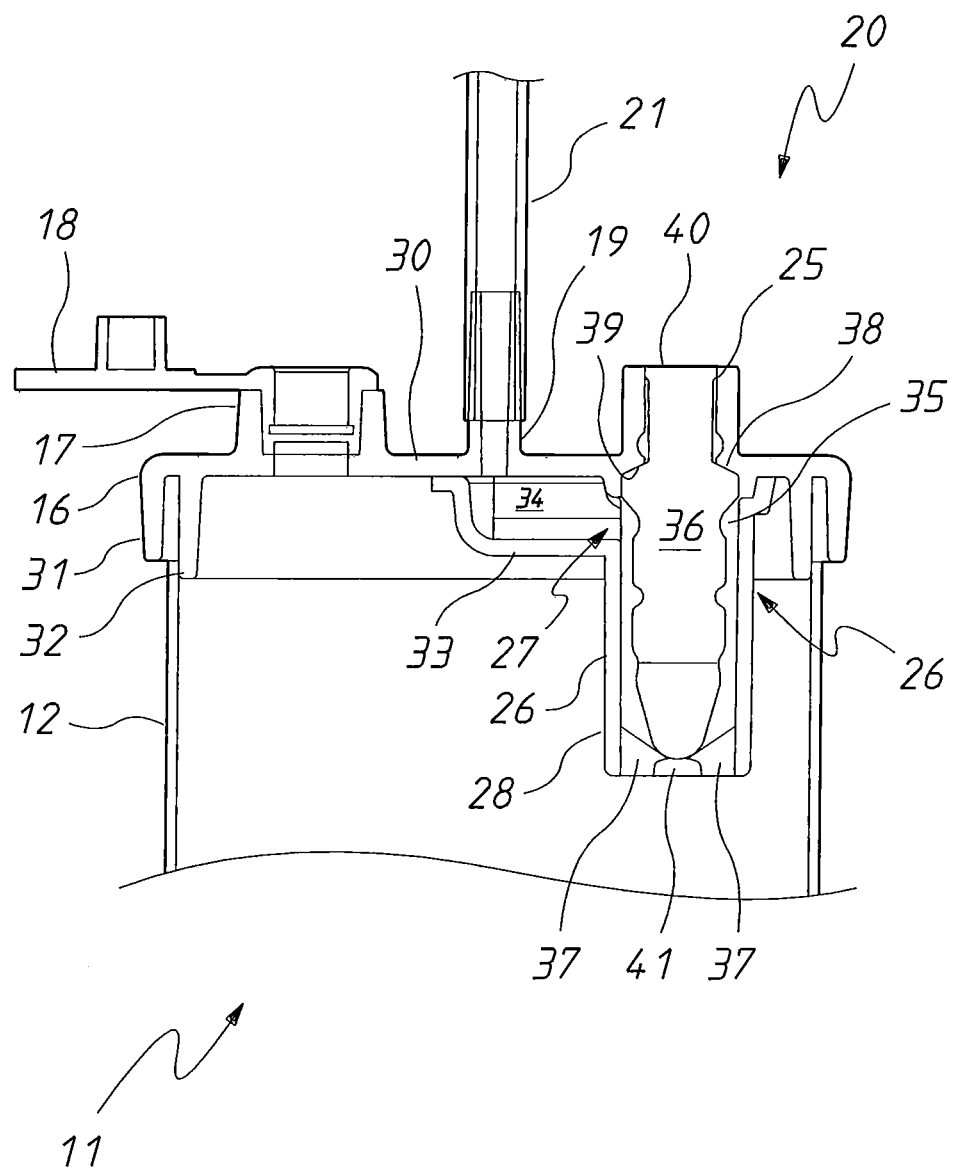
FIG. 7 is a schematic sectioned side elevation of the combination of FIG. 4.

The injection port 20 includes an inlet in the form of an injection passage 25 via which a liquid is injected into the injection port 20. Typically the liquid being injected is a medication. The injection port 20 could be constructed substantially as described in U.S. Pat. No. 5,782,816, in particular an injection port as illustrated in FIG. 7 of this USA Patent. The injection port 20 has a hollow body 26 enclosing a chamber that receives liquid from the tube 21 as well as the passage 25. In particular there is extending from the body 26 an inlet 27 from which the tube 21 extends.

Located within the chamber enclosed by the body 26 is a movable closure member that is resiliently urged to close the passage 25. A male luer fitting is inserted in the passage 25 to displace the closure member to provide for the delivery of a liquid to the interior (chamber) of the body 12 for delivery to the burette 11. The male luer fitting may be in accordance with International Standard ISO 594-1:1986, preferably ISO 594-2:1998. To ensure all medication is delivered, a syringe having the luer fitting is operated to draw liquid in from within the body 12, this liquid would be in particular liquid from the reservoir 22. This is then again delivered to the interior of the body 12 by operation of the syringe. Accordingly, the syringe and injection port 20 are flushed with liquid from the reservoir 22. Liquids delivered via the inlet passage 25 and inlet 27 are then delivered to the patient via the outlet 13.

In the embodiment of FIG. 1, the injection port 20 is fixed relative to the cap 16 by having an outlet 28 extend into and secured to the inlet 19. In the embodiments of FIGS. 2 and 3, a tube 29 connects the outlet 28 with the inlet 19.

In the embodiment of FIG. 3, the inlet 27 is axially aligned with the outlet 28 as opposed to the embodiments of FIGS. 1 and 2 in which the inlet passage 25 is axially aligned with the outlet 28. In the embodiments of FIGS. 1 and 2, the inlet 27 extends generally transverse relative to the passage 25 and outlet 28 and preferably at an acute angle relative thereto.

Figures 4, 5, 6:
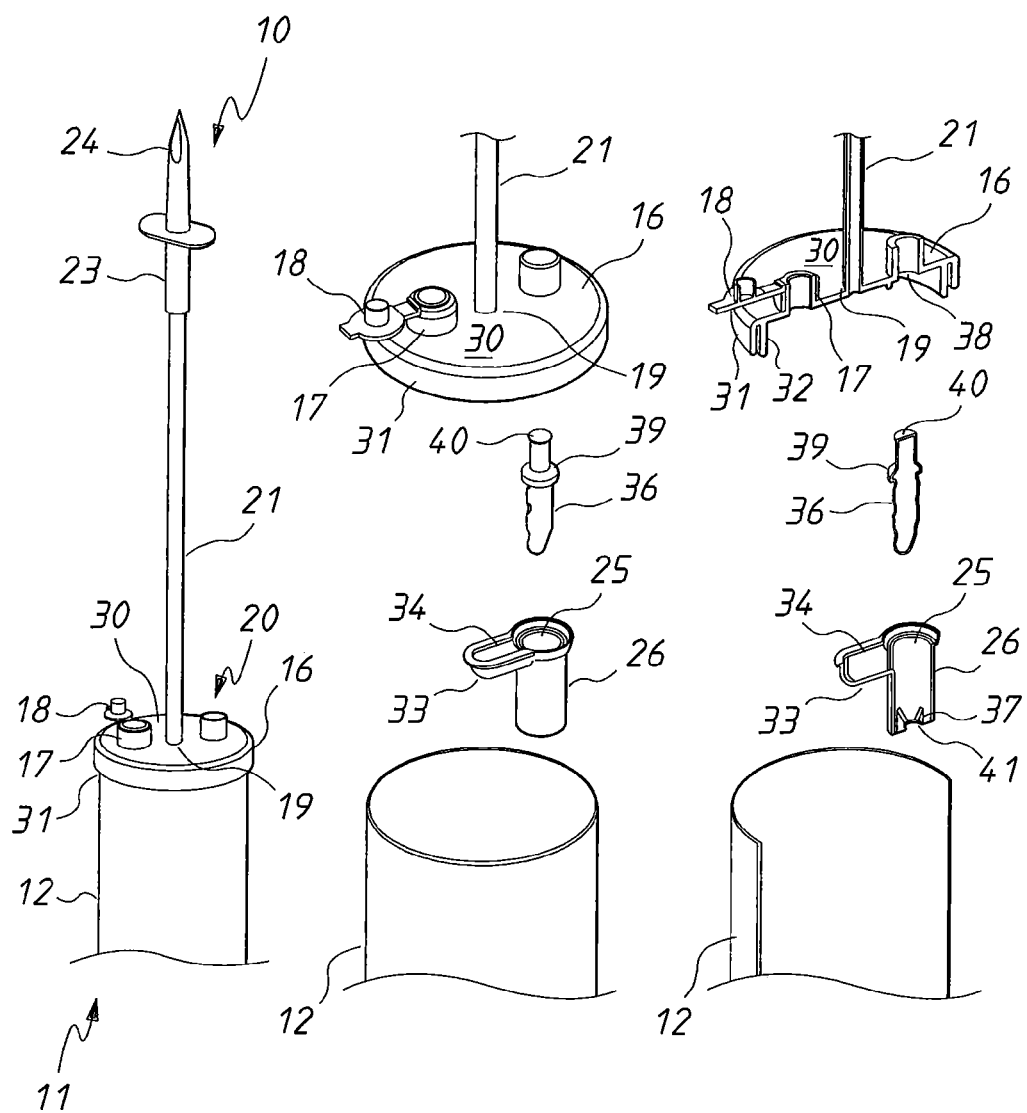
FIG. 4 is a schematic pictorial view of a still further modification of the combination of claim 1.
FIG. 5 is a schematic pictorial parts exploded perspective view of the combination of FIG. 4.
FIG. 6 is a schematic sectioned pictorial view of the combination of FIG. 5.

In the embodiment of FIGS. 4 to 7, the injection port 20 is mounted in the cap 16. The cap 16 has an upper part 30 from which there depends a pair of annular flanges 31 and 32 between which the body 12 is located. Formed integral with the upper part 30 is the inlet 19 to which the tube 21 is attached. However in this embodiment there is formed integral with the cap 16 a duct 33 providing a passage 34 that is in communication with the inlet 19 so as to receive liquid from the tube 21. As an alternative embodiment, the duct 33 may be formed integral with the body 26. This construction is best seen in FIGS. 5 and 6. The passage 34 forms part of the inlet 27 of the injection port 20. The inlet 27 communicates with the internal chamber 35 of injection port 20 so that liquid from the tube 21 can be delivered to the outlet 28 of the injection port 20. Located internally of the chamber 35 is a resiliently deformable closure member 36. The closure member 36 is compressed between flanges 37 and an annular valve seat 38 of the body 26 so that an annular sealing surface 39 of the member 36 is urged into sealing contact with the seat 38 to close the passage 25. When the fitting of a syringe is applied against the upper end surface 40 of the member 36 and pressed there against, the member 36 resiliently deforms so that the surface 39 moves away from the surface 38. This allows the syringe to be operated to deliver the medication to the interior of the body 12 wherefrom it flows via the outlet 13 to the tube 14. The opening 41 provides an inlet to the interior of burette 11. In this regard it should be appreciated that liquid from the tube 21 flows via the passage 34 through the chamber 35 to exit via the opening 41. Once the syringe has been operated, the plunger of the syringe can be withdrawn so that liquid from the chamber 35 may be drawn back up into the syringe. This syringe withdrawal process of returning fluid is preferably conducted while there is a steady flow of liquid from the reservoir 22 through the chamber 35. Further operation of the syringe returns the liquid to the chamber 35. Withdrawn fluid will then preferentially be taken from incoming fluid from the passage 34, rather than air from the outlet 28. This operation flushes not only the syringe but the interior of the injection port 20.

The invention claimed is:

1. In combination a burette and an injection port:
    said burette having an interior with an inlet via which a first liquid is delivered to the burette interior and an outlet via which an outward liquid is to be delivered to a patient, wherein the first liquid is received from a tube having an end portion connected to a reservoir;
    said injection port being fixed to the burette, said injection port having:
        a body enclosing a port chamber;
        a first inlet for receiving from the tube the first liquid and to deliver the first liquid to said port chamber;
        a duct extending from said first inlet, said duct providing a passage between said tube and said first inlet;
        an injection inlet for receiving a second liquid, from a source external the injection port, into said port chamber and delivering the second liquid to said chamber; and
        an outlet for delivering the first and second liquids into said interior via the burette inlet;
    wherein said body enclosing said port chamber is positioned within a cap atop said burette;
    wherein said injection inlet includes a movable closure member operable to be opened for the delivery of said second liquid to said chamber but urged to a closed position closing said port chamber; and
    wherein said injection inlet is configured to allow an amount of said first liquid to be drawn from within said port chamber and re-delivered back into said port chamber.

2. The combination of claim 1, wherein said burette has a hollow body providing said interior to receive the first and second liquids, and an upper part closing said body provides said cap, with said injection port being incorporated in said upper part.

3. The combination of claim 2, wherein said upper part includes the duct to be connected to said tube and in communication with said first inlet for the delivery of said first liquid to said port chamber.

4. In combination a burette and an injection port;
    said burette having an interior and a burette inlet via which a first liquid is delivered to the interior, an outlet via which an outward liquid is to be delivered to patient, and an upper portion providing a cap;
    said injection port being incorporated in said cap so as to be fixed to the burette, and having:
        a body enclosing a port chamber
        a first inlet for receiving the first liquid from the burette inlet and to deliver the first liquid to said chamber;
        a duct extending from said first inlet, said duct providing a passage between a tube and said first inlet;
        an injection inlet for receiving a second liquid, from a source external the injection port, into said chamber and delivering the second liquid to said port chamber, and an outlet for delivering the first and second liquids into said interior, via the burette inlet;
    wherein said body enclosing said port chamber is positioned within said cap atop said burette;
    wherein said injection inlet includes a movable closure member operable to be opened for the delivery of said second liquid to said port chamber but urged to a closed position closing said port chamber; and
    wherein said injection inlet is configured to allow an amount of said first liquid to be drawn from within said port chamber and re-delivered back into said port chamber.

* * * * *